United States Patent [19]

Nguyen et al.

[11] Patent Number: 5,252,832
[45] Date of Patent: Oct. 12, 1993

[54] METHOD OF USING THERMAL NEUTRONS TO EVALUATE GRAVEL PACK SLURRY

[75] Inventors: Philip D. Nguyen; Ronnie J. Buchanan; Jimmie D. Weaver, all of Duncan, Okla.

[73] Assignee: Halliburton Company, Duncan, Okla.

[21] Appl. No.: 847,507

[22] Filed: Mar. 6, 1992

[51] Int. Cl.$^5$ .......................................... G01N 23/00
[52] U.S. Cl. ............................. 250/390.01; 250/269; 250/390.04; 250/390.06
[58] Field of Search ..................... 250/390.06, 390.05, 250/390.04, 390.01, 269

[56] References Cited

U.S. PATENT DOCUMENTS

| | | | |
|---|---|---|---|
| 4,057,729 | 11/1977 | Hewitt | 250/390.06 |
| 4,302,669 | 11/1981 | Allen et al. | 250/264 |
| 4,414,472 | 11/1983 | Watt | 250/359.1 |
| 4,423,323 | 12/1983 | Ellis et al. | 250/264 |
| 4,424,444 | 1/1984 | Smith, Jr. et al. | 250/270 |
| 4,459,480 | 7/1984 | Dimon | 250/269 |
| 4,499,380 | 2/1985 | Aggour et al. | 250/390.04 |
| 4,587,423 | 5/1986 | Boyce | 250/269 |
| 4,625,110 | 11/1986 | Smith, Jr. | 250/269 |
| 4,625,111 | 11/1986 | Smith, Jr. | 250/270 |
| 4,631,405 | 12/1986 | Smith, Jr. | 250/266 |
| 4,638,161 | 1/1987 | Smith, Jr. et al. | 250/269 |
| 4,641,028 | 2/1987 | Taylor et al. | 250/266 |
| 4,910,397 | 3/1990 | Mills, Jr. et al. | 250/264 |
| 4,947,040 | 8/1990 | Mahdavi et al. | 250/266 |
| 5,083,029 | 1/1992 | Buchanan | 250/390.05 |
| 5,099,124 | 3/1992 | Benson | 250/357.1 |

FOREIGN PATENT DOCUMENTS 1-68609  3/1989  Japan .................. 250/390.06

OTHER PUBLICATIONS

Pp. 129–133 containing section 7.4.1 on neutron–neutron-logging of an unknown book, believed published more than one year prior to Dec. 1991.
"Model 2500X Coke Moisture System" for Kay-Ray Inc. (1982).
"Model 4100F Coke Drum Level Measurement System" for Kay-Ray Inc. (1982).
"Level Measurements Eased With Hand-Held Instrument" printed in Chemical Processing publication, dated Nov. 1986.
"6500 Mass Flowmeter—The Unique New System That Simultaneously Measures Density, Flow and Mass Flow" for Kay Ray Inc. (1980).
"Mechanics of Gravel Placement and Packing: A Design and Evaluation Approach," M. A. Wahlmeier and P. W. Andrews, SPE Production Engineering, pp. 69–82 (Feb. 1988).
Dowell Schlumberger leaflet entitled "Sand Control, PacCade Placement Software System" (believed to be before Oct. 1990).
SPE 19753 entitled "Numerical Simulation of Gravel Packing," P. H. Winterfeld and D. E. Schroeder, Jr. (1989).

Primary Examiner—Constantine Hannaher
Attorney, Agent, or Firm—Robert A. Kent

[57] ABSTRACT

A method of evaluating a gravel pack slurry uses a fast neutron source and a thermal neutron detector to produce responses from which gravel settling rate, packing efficiency, gravel concentration, porosity and density can be determined. The method can be applied to either static or dynamic slurries in either a laboratory test environment or an actual well environment.

8 Claims, 5 Drawing Sheets

METHOD OF USING THERMAL NEUTRONS TO EVALUATE GRAVEL PACK SLURRY

BACKGROUND OF THE INVENTION

This invention relates generally to a method of evaluating gravel pack slurry (including a resultant gravel pack) and more particularly, but not by way of limitation, to a method of determining one or more characteristics about a gravel pack slurry under dynamic conditions wherein the slurry is flowing relative to one or more fast neutron sources and thermal neutron detectors.

In some formations into which a well has been drilled for producing oil or gas, sand will be produced along with the oil or gas. This is not desirable because sand can cause problems such as equipment damage and reduced production of the oil or gas. One way to inhibit sand production is to pump gravel (i.e., typically larger grained sand) down into the well so that it packs tightly in the annular space between a screen and the formation (or casing cemented to the formation) to minimize the movement of sand grains produced from the formation during the production of oil or gas. The effectiveness of this treatment can be critical to the viability of the well; therefore, proper planning and execution of a gravel pack job are important.

To properly plan at least some types of gravel pack jobs, tests of different fluids should be performed in a laboratory to determine which fluid appears to be best for the particular well environment. These fluids are typically slurries of gravel mixed in a carrier liquid containing various constituents known in the art (although "sand" is commonly the packing component of such a slurry, the term "gravel" will be used herein to be consistent with the terminology "gravel pack" and to be distinguished from the "sand" which flows out of the formation with the oil or gas and which is to be blocked by the gravel pack).

Heretofore, gravel pack slurries have typically been tested in a large physical model or via computer modeling. The former is expensive and does not produce all the information desired, and the latter does not yield direct results of what is actually happening in a slurry. One particular shortcoming of the physical model is that the void spaces in the gravel pack cannot be determined unless the model is made with a transparent material, such as plastic or glass; but such a transparent model can have temperature and pressure limitations precluding simulations at actual elevated downhole temperatures and pressures. Even if the void spaces could be seen, there would not be a quantitative analysis of the gravel pack. Where the void spaces are, and their quantification, are important information because a successful gravel pack depends on the percentage of void space which exists in the pack. That is, the less void space there is, the less chance there is for sand to be produced with the oil or gas. Furthermore, physical models that derive evaluation data from pressure transducer measurements can have limited spatial resolution and accuracy.

Determining whether a planned gravel pack job is being successfully performed has been even more elusive than properly planning a gravel pack job. That is, we are not aware of a method which monitors what actually happens as a gravel pack slurry is pumped into a well and which provides data for indicating characteristics of the actual gravel pack formed (e.g., packing efficiency, gravel concentration, porosity, density, patterns of gravel packed in the well, and gravel settling rate).

In view of the aforementioned shortcomings, there is the need for a method for evaluating a gravel pack slurry, whether in a laboratory test environment or down in an actual well environment. Such a method should directly test the slurry in that it should provide direct responses to an actual slurry in its displacement in a pipe or annulus. For enhanced resolution, it should be capable of evaluating multiple discrete volumes of the overall volume of slurry. More particularly, the method should be capable of providing information from which packing efficiency, gravel concentration, porosity, density, and patterns of gravel packed in the well, and gravel settling rate can be determined.

SUMMARY OF THE INVENTION

The present invention overcomes the above-noted and other shortcomings of the prior art, and meets the aforementioned needs, by providing a novel and improved method of evaluating a gravel pack slurry (which term encompasses both the fluid mixture and the resultant pack). In a particular implementation, the method determines a sand (i.e, gravel) settling rate for a gravel pack slurry; however, other characteristics such as packing efficiency, gravel concentration, porosity, density, and patterns of gravel packed in the well can be determined using the method of the present invention.

The present invention enables such information to be obtained about a gravel pack slurry through direct responses to an actual slurry. The slurry can be either in a laboratory or a well, and it can be either stationary or flowing and at any orientation (e.g., horizontal or vertical). In whatever mode, the slurry can be evaluated over multiple discrete volumes of the overall volume so that relative locations of gravel throughout the sensed volumes, and the shifting of the gravel within the sensed volumes, can be determined, thereby enabling fine or detailed resolutions to be obtained.

The method of the present invention comprises: placing the gravel pack slurry in a channel; emitting fast neutrons at the placed slurry from outside the channel so that fast neutrons are thermalized in response to the gravel pack slurry; detecting from outside the channel neutrons which have been thermalized in the gravel pack slurry in the channel; providing a count representative of the detected neutrons; and determining a characteristic of the gravel pack slurry in response to the count.

The method of the present invention can also be defined as comprising: determining, at a plurality of locations, thermal neutron responses of the gravel pack slurry, which includes gravel and a carrier medium, to fast neutrons emitted into the gravel pack slurry; and comparing the responses to determine the relative distribution of gravel and carrier medium at the plurality of locations.

A particular implementation of the present invention, wherein a gravel settling rate is determined, comprises: (a) emitting fast neutrons into the gravel pack slurry so that fast neutrons are thermalized in response to hydrogen in the gravel pack slurry, wherein the gravel and carrier medium are initially mixed within the gravel pack slurry; (b) detecting thermalized neutrons from the gravel pack slurry; (c) continuing steps (a) and (b) from a first time, at which a substantially constant relatively low level of thermalized neutrons is detected, until a second time, at which a substantially constant relatively high level of thermalized neutrons is detected; and (d) determining the gravel settling rate in response to the difference between the first time and the second time.

Therefore, from the foregoing, it is a general object of the present invention to provide a novel and improved method of evaluating a gravel pack slurry. Other and further objects, features and advantages of the present invention will be readily apparent to those skilled in the art when the following description of the preferred embodiments is read in conjunction with the accompanying drawings.

DETAILED DESCRIPTION OF PREFERRED EMBODIMENTS

The method of the present invention uses one or more sources of fast neutrons to emit the neutrons into a gravel pack slurry, and it uses one or more thermal neutron detectors to detect thermal neutrons produced by the interaction of fast neutrons with hydrogen atoms in the slurry. Such sources, detectors and the aforementioned interaction and reduction of fast neutrons to thermal neutrons are well known. This same concept is used in a different method in U.S. Pat. No. 5,083,029 which is assigned to the assignee of the present invention and incorporated herein by reference. Using this concept, if relatively more thermal neutrons are detected, this indicates there is relatively more hydrogenous material within a particular monitored volume as compared to sensing a lesser number of thermal neutrons.

Figure 1A:
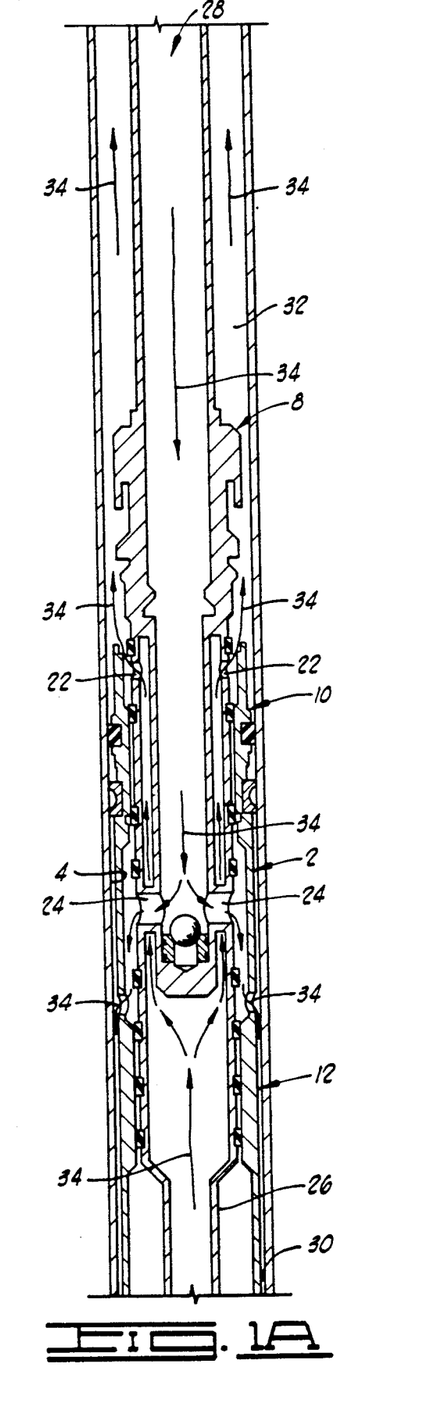
FIGS. 1A and 1B depict one position of a known tool relative to a known gravel pack assembly located in a well wherein the method of the present invention can be used.
Figure 1B:
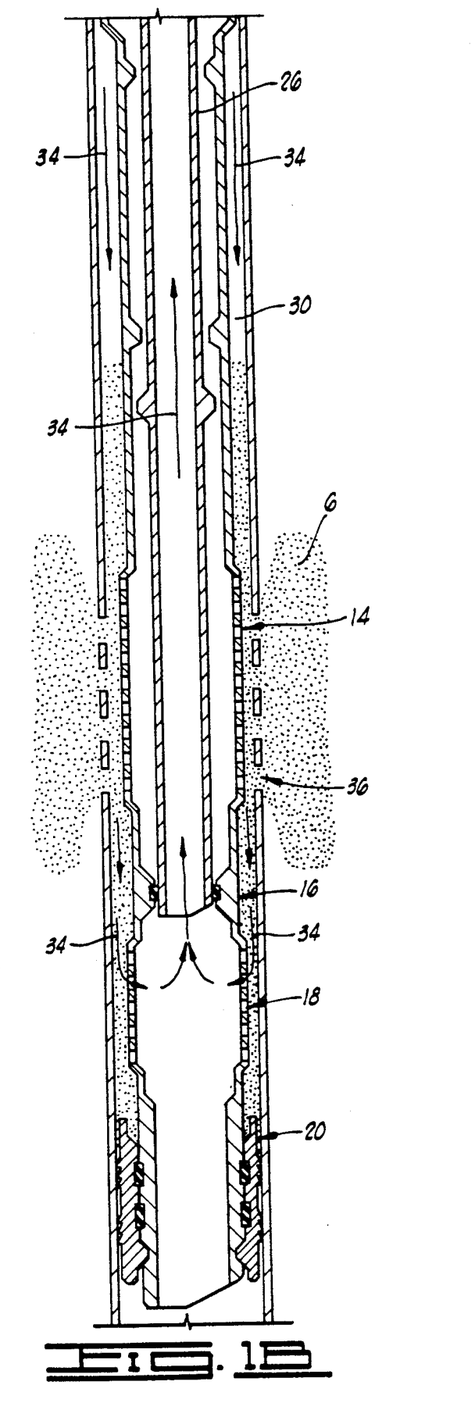

Referring to FIGS. 1A and 1B, a gravel packer assembly 2 is fixed in a well 4 across a formation 6 containing oil or natural gas and sand which is to be blocked by the gravel packing system. Positioned in the assembly 2 is a tool 8 that can be moved longitudinally relative to the assembly 2 by lowering or raising a pipe string (not shown) to which the tool 8 is connected and which extends to the surface as known in the art. Different relative positions between the assembly 2 and the tool 8 provide different flow channels as known in the art.

The gravel packer assembly 2 includes a gravel packer 10, a ported flow sub 12, a production screen 14, an O-ring sub 16, a telltale screen 18 and a sump packer 20. These are conventional pieces of equipment connected in a conventional manner. For example, the gravel pack packer 10 can be implemented by an OTIS VERSA-TRIVE TM packer.

The tool 8 is likewise conventional, such as an OTIS/VANN multi-position tool. This tool includes upper ports 22, lower ports 24 and a wash pipe 26.

When the tool 8 is positioned relative to the gravel packer assembly 2 as shown in FIGS. 1A and 1B, the system is in a lower circulating mode. In this mode, a gravel pack slurry can be pumped down the pipe string, through an axial passageway 28 of the tool 8, out the lower ports 24 and the ported flow sub 12, down an annulus 30, in through the telltale screen 18, around and into the lower end of the wash pipe 26, out the upper ports 22 and up an annulus 32. This flow is indicated by the arrows 34. During this flow, gravel is placed in at least a portion of the annulus 30 and out perforations 36 into the formation 6 (FIG. 1B).

The gravel pack slurry in its sense as a fluid mixture used in the environment illustrated in FIGS. 1A and 1B typically includes a determined quantity of gravel (usually referred to as "sand" but referred to herein as "gravel" as explained hereinabove) mixed in a carrier fluid comprising a number of known constituents. The constituent of particular interest to the present invention is water because it is the predominant or primary source of hydrogen atoms in the overall slurry. Although there may be other sources of hydrogen in the slurry or other parts of the downhole environment, such can be accounted for by appropriate calibration readily known in the art.

As has been previously explained, it is desirable to evaluate the gravel pack slurry both as it is pumped downhole in a flowing or dynamic condition as well as in a static or stationary condition wherein evaluation of the resulting gravel pack, such as illustrated by the dotted portion of FIG. 1B and encompassed by the term gravel pack slurry as used herein, can be determined. Preferably, the evaluation should provide a quantified analysis of the slurry and in particular the local packing efficiency, gravel concentration, porosity, density, pattern of gravel packed in the well bore, and gravel settling rate. Depending upon the particular utilization of the present invention, even the location of void spaces in the packed gravel can be determined. These characteristics can be determined from the count of thermal neutrons detected by a thermal neutron detector. The thermal neutron detector is preferably located radially inwardly of the substantially annular gravel pack depicted in FIG. 1B when the gravel pack slurry in the annulus is to be evaluated (the present invention can, in general, be used to evaluate the slurry in a particular channel in which it is placed, whether the channel is defined inside the inner pipe or in the annulus 30 as shown in the illustration of FIGS. 1A and 1B). Preferably a corresponding source of fast neutrons would be positioned with the detector. Multiple sources and/or detectors can be used as will be further explained herein below.

Figure 2:
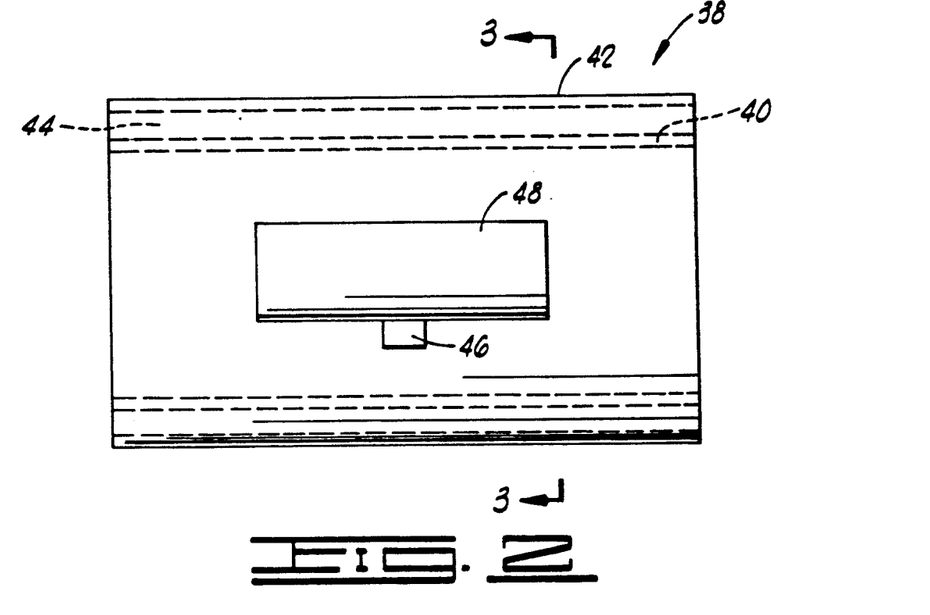
FIG. 2 is a side view of a tubular test equipment for implementing the method of the present invention in a laboratory test environment.
Figure 3:
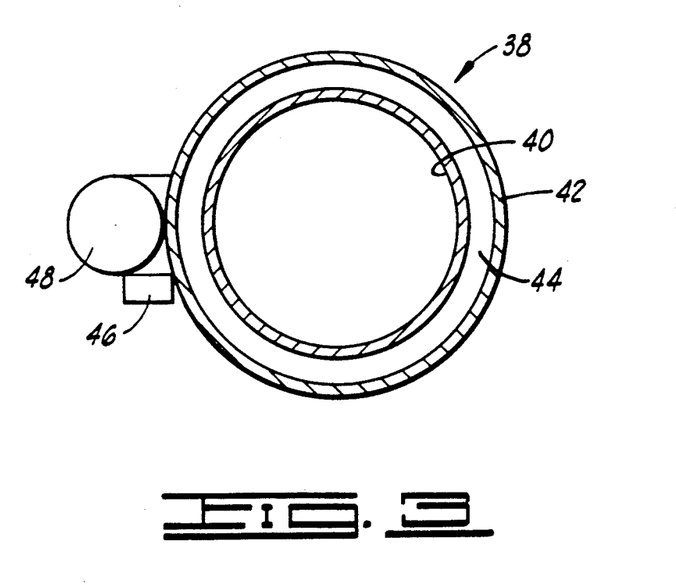
FIG. 3 is a cross-sectional view of the tubular test equipment taken along line 3—3 in FIG. 2.
Figure 8:
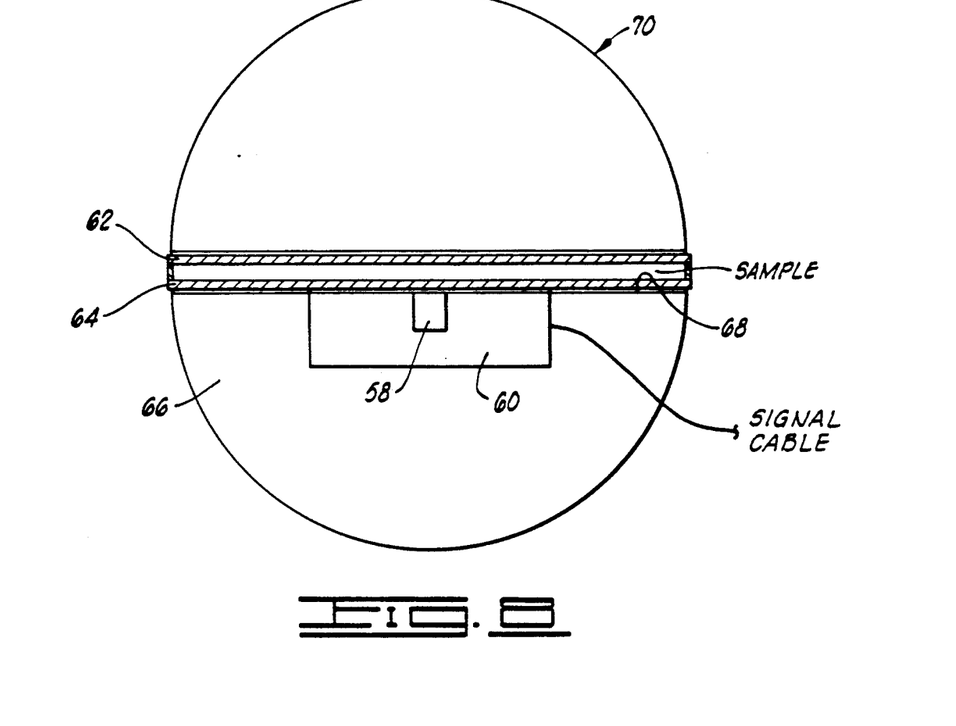
FIG. 8 is a top cross-sectional view of a contemplated test model for measuring sand concentration and settling rate in accordance with the present invention.

The method of the present invention can also be used in a laboratory test environment as well as in the previously illustrated actual downhole environment. Referring to FIGS. 2 and 3, an annular lab equipment 38 is illustrated (shown without shielding to focus on the channel defining structure, the source, and the detector; however, biological shielding should be used, as depicted in the embodiment of FIG. 8). Equipment 38 simulates a downhole annulus by centralizing an inner pipe 40 concentrically within an outer pipe 42 so that an annulus 44 exists between the outer surface of the pipe 40 and the inner surface of the pipe 42. By way of example, the pipes can have a 0.25" (inch) wall thickness, and the pipe 40 can have an outer diameter of about 6.25" (inches) and the pipe 42 can have an outer diameter of approximately 7". These dimensions would give the annulus 44 a 0.5" inch thickness.

The ends of the pipes 40, 42 can be opened or closed. The ends would be closed if a static volume of slurry were to be tested (static except for migration of gravel due to settling prior to an ultimate pack state being reached). If a flowing slurry were to be tested, one end would be open to receive a continuously pumped flow of the slurry; the other end would be open to return the flow of slurry to the source tank, or it could be connected with a screen so only gravel-free fluid filters out. The slurry would reside in or flow through the annulus 44 to simulate residence or flow in the actual annulus 30 depicted in FIGS. 1A and 1B.

To emit fast neutrons into the tested slurry, a known source 46 of fast neutrons is disposed adjacent the outer surface of the pipe 42. Located adjacent the source 46 is a known type of thermal neutron detector 48. Non-limiting examples of a source 46 are ones which include either americium-beryllium or californium as the source material For example, a 250-millicurie (mCi) americium-beryllium (AmBe) material from Gammatron in Houston, Texas could be used. An example of a particular detector 48 is a two-inch by six-inch helium-3, 4-atmosphere thermal neutron detector from Texas Nuclear. Shielding and focusing materials can be used as needed and as would be readily understood in the art.

Figure 4:
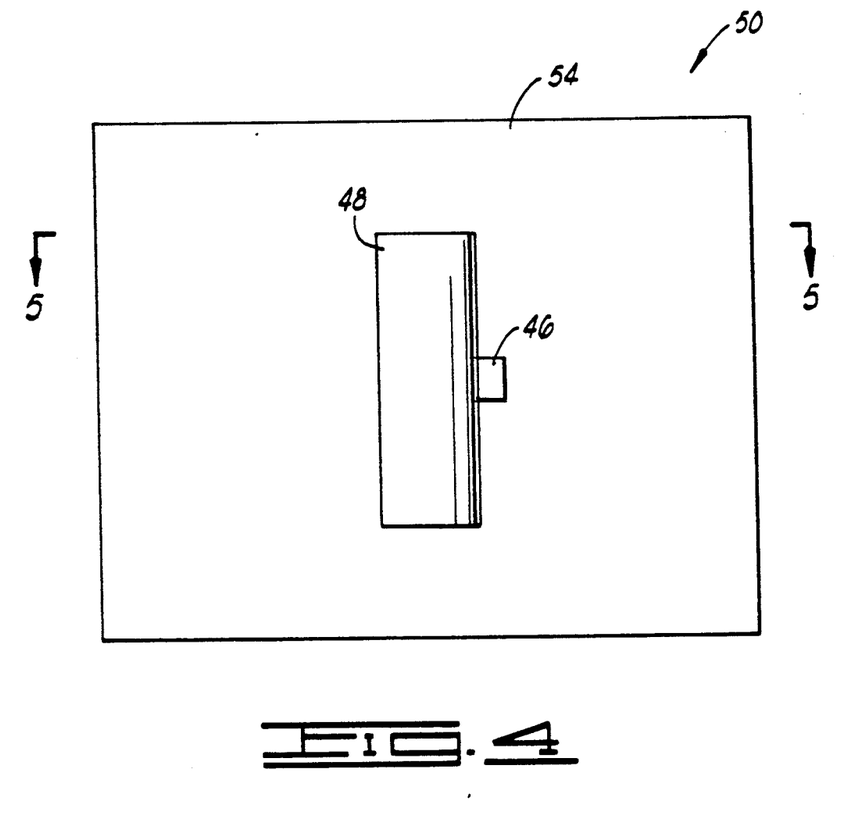
FIG. 4 is an elevational view of a flat plate test equipment for implementing the method of the present invention in a laboratory test environment.
Figure 5:
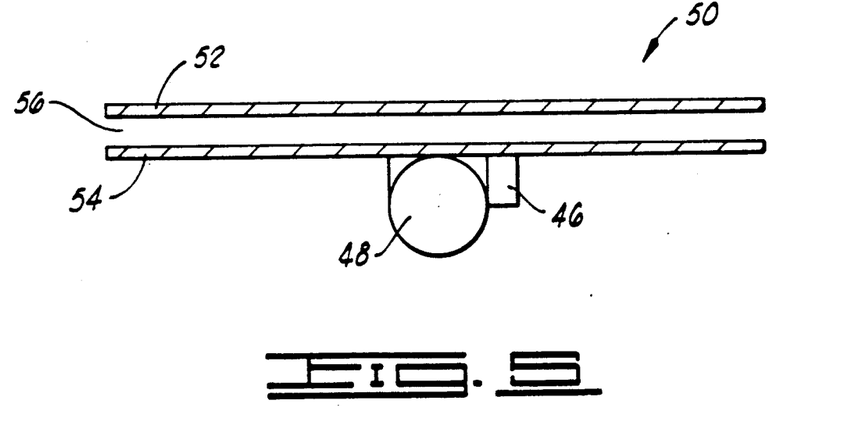
FIG. 5 is a cross-sectional view of the flat plate test equipment taken along line 5—5 in FIG. 4.

Referring to FIGS. 4 and 5, another type of laboratory equipment is illustrated (as in the prior illustration, shown without recommended shielding as would be apparent). Flat plate equipment 50 includes two flat plates 52, 54 (12" square in a particular implementation) spaced a suitable distance, such as 0.5", to simulate an actual annulus such as those shown in FIGS. 1-3. This space is identified by the reference numeral 56 in FIG. 5. A fast neutron source and a thermal neutron detector are connected to the plate 54. These can be the same as those shown in the embodiment of FIGS. 2 and 3 as indicated by the same reference numerals. The equipment 50 shown in FIGS. 5 and 6 will typically be vertically oriented and contain slurry in the space 56 (the present invention, however, is applicable to any orientation, whether vertical, horizontal or otherwise). The space 56 can be closed at both sides and top and bottom to retain a static volume of slurry which has been pumped in. Although the slurry in such arrangement would be static, relative movement or settling of the gravel within the slurry would not be inhibited. The space 56 can also be used for dynamic testing with flow in and out as described above with reference to the embodiment of FIGS. 2 and 3.

Regardless of the operating conditions, the source 46 and detector 48 are used to track gravel settling over time. Considering a static condition, for example, as the neutron source 46 is directed at a well mixed gravel pack slurry in the space 56, the number of neutrons thermalized will be low because there will be a relatively high gravel density within the volume covered by the source 46 and detector 48. At a later time, as more gravel particles have settled, the density in the monitored region will have decreased so that the number of neutrons thermalized will have increased. Accordingly, the gravel settling rate can be determined for the time period required for the thermal neutron count rate to increase from a constant relatively low level to a constant relatively higher level. This corresponds to a measurable depth of gravel free supernatant layer, independent of fluid viscosity. The effects of polymer concentration within the carrier fluid of the slurry, the viscosity, the gravel concentration, the particle size, and pressure and temperature on the settling rate can all be obtained by utilizing this method.

Figure 6:
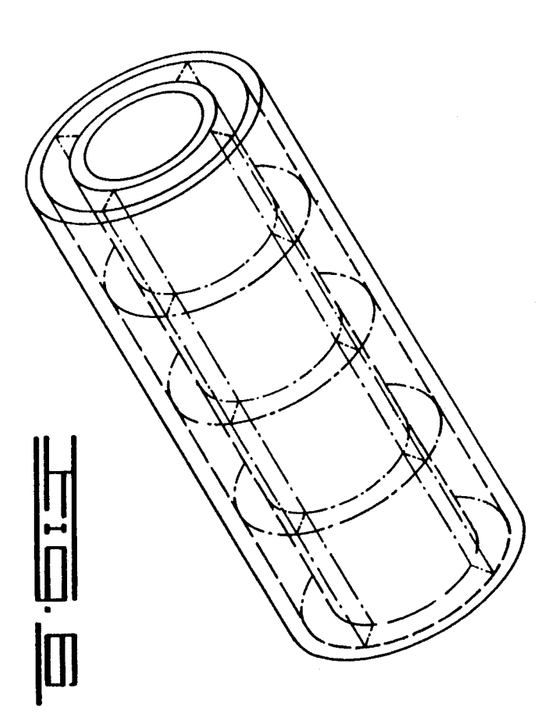
FIG. 6 is a perspective view of an annulus with longitudinal and angular markings representing discrete volumes of the annulus where separate readings can be taken by the method of the present invention.

The foregoing illustrations have been depicted with a single fast neutron source and a corresponding single thermal detector fixed at a single location. Such a combination of one source and a corresponding detector is preferred to minimize interference or false readings; however, such single source and detector combination can be moved relative to the annulus and slurry contained therein or, alternatively multiple sources and detector combinations can be used. It is also contemplated that a single source with multiple detectors can be used. These variations can be applied to cover any number of and any array of discrete volumes of the overall volume of slurry. An example of such discrete volumes is illustrated in FIG. 6. One or more of these volumes could be monitored by a single source and detector combination moved angularly (circumferentially) and/or linearly (longitudinally), or a combination thereof, or by fixed sets of sources and/or detectors dedicated to each selected volumetric portion to be monitored. It is also contemplated that a single source could be used with multiple detectors associated with each desired volumetric portion. The sources and/or detectors can be placed either radially inwardly or radially outwardly of an annular channel, and radially outwardly of a pipe defining a full cylindrical channel (i.e., one with a continuous cross section), in which the slurry is placed for monitoring. Either both source and detector can be on the same side of the channel, or one on one side and the other on the other side of the channel. The resolution to which the present invention can evaluate a gravel pack slurry depends at least in part on the number and size of the volumetric portions monitored and, more particularly, on the size of the thermal neutron detectors relative to the void spaces.

When multiple locations are monitored, the method of the present invention comprises: determining, at such plurality of locations, thermal neutron responses of the gravel pack slurry to fast neutrons emitted into it; and comparing the responses to determine the relative distribution of gravel and carrier medium at the plurality of locations. The thermal responses are obtained using one or more fast neutron sources and thermal neutron detectors as previously described. The responses can be compared in a conventional computer, for example. This can be readily implemented by a program to compare one value to another, with a relatively higher thermal neutron response indicating relatively more hydrogenous material (and thus relatively less gravel).

Summarizing from the foregoing, the method of the preferred embodiments is used with a gravel pack slurry placed in a channel. The channel can be in an actual well or test equipment, and it can be in a pipe or an annulus (or a simulation thereof as illustrated in the equipment 50 of FIGS. 4 and 5). Fast neutrons are emitted at the slurry from outside the channel so that fast neutrons are thermalized in response to the gravel pack slurry (specifically, by the hydrogen atoms encountered by the fast neutrons). The method further comprises: detecting from outside the channel neutrons which have been thermalized in the gravel pack slurry in the channel; providing a count representative of the detected neutrons; and determining a characteristic of the gravel pack slurry in response to the count. "Outside the channel" as used in the preceding description encompasses both radially inwardly of and radially outwardly of an annulus and radially outwardly of a continuous cross section channel as defined inside a single pipe.

Specifically to determine a gravel settling rate for a gravel pack slurry, the present invention comprises: (a) emitting fast neutrons into the gravel pack slurry so that fast neutrons are thermalized in response to hydrogen in the gravel pack slurry, wherein the gravel and carrier medium are initially mixed within the gravel pack slurry; (b) detecting thermalized neutrons from the gravel pack slurry; (c) continuing steps (a) and (b) from a first time, at which a substantially constant relatively low level of thermalized neutrons is detected, until a second time, at which a substantially constant relatively high level of thermalized neutrons is detected; and (d) determining the gravel settling rate in response to the difference between the first time and the second time. That is, at the aforementioned first time, there is relatively more gravel in the evaluated volume than there is at the second time. The difference between the thermal neutron counts at these two times represents the difference in gravel within the volume so that this difference divided by the time difference represents gravel settling rate. The gravel settling rate obtained can be used in examining the rheological properties of the carrier fluids. Knowing how these fluids behave under certain geometrical and mechanical conditions allows optimization as well as preventing undesired results.

Equations by which the specific characteristics are derived in correlation to the count of thermal neutrons provided by each of the thermal neutron detectors are obtained from empirical analysis of calibration data and obtained data. A calibration curve is established based on known geometry and quantities of water and gravel (i.e., slurry concentration) prior to the actual measurements and ultimate calculations.

In a preferred embodiment calibration, a gravel pack slurry is prepared with each of the following known: concentration of gravel, concentration of polymer, whether linear or crosslinked polymer, and gravel particle size. This slurry is pumped at a constant flow rate into the channel or channels where it is to be evaluated. The thermal neutron response is measured until consistent readings with minimum fluctuations are obtained. The foregoing steps are repeated for different gravel concentrations, different polymer concentrations, different flow rates and different particle sizes. The obtained measurements are used to establish curves of thermal neutron readings versus water content at known flow rate, particle size and polymer concentration. These curves can then be used to define equations correlating thermal neutron counts to the various parameters (e.g., gravel concentration) set forth hereinabove as will be readily apparent to those skilled in the art.

The following examples further explain the foregoing description of the present invention.

Known mixtures of gravel (sand) and gravel packing gel (i.e., the carrier medium) were put in between two 0.025" thick steel plates that were separated by a 0.5" gap. A 269 mCi AmBe neutron source, average neutron energy of 4.5 Mev, was mounted on the outside of one of the steel plates and a 2"×6" He-3 neutron detector at 4 atm. was mounted next to the neutron source on the same side of the steel plate. A thickness of poly-boron shielding of at least 4" surrounded the outside of both steel plates for biological shielding purposes. A lining of 0.020" cadmium metal was placed on the inside surfaces of the poly-boron shielding to absorb backscattered neutrons from the poly-boron. The count rate of the detector was then recorded as a function of gravel concentration, which was previously determined by weight and volume measurements. The gravel concentrations used were 0, 2, 4, 8, 12, 18, and 24 pounds of gravel per gallon of gel.

Experiments were also conducted to determine the spatial resolution of the test system. This consisted of positioning a 0.5" thick by 1" wide slab of paraffin in the 0.5" gap at 1" intervals and recording the resulting count rate as a function of position.

For the apparatus used in this experimental setup the response function was approximated by the equation:

$$Y = 7.65X + 902 \; cps,$$

where Y is gross counts per second, X is the concentration of gel by volume (from which the gravel concentration can be determined), and 902 cps (counts per second) is the average count rate with the apparatus empty.

An apparatus was also utilized that had a 0.25" gap for the sample and the same experiment conducted as above. The error in detecting changes in gravel concentrations was greater because the amount of material present was less.

Figure 7:
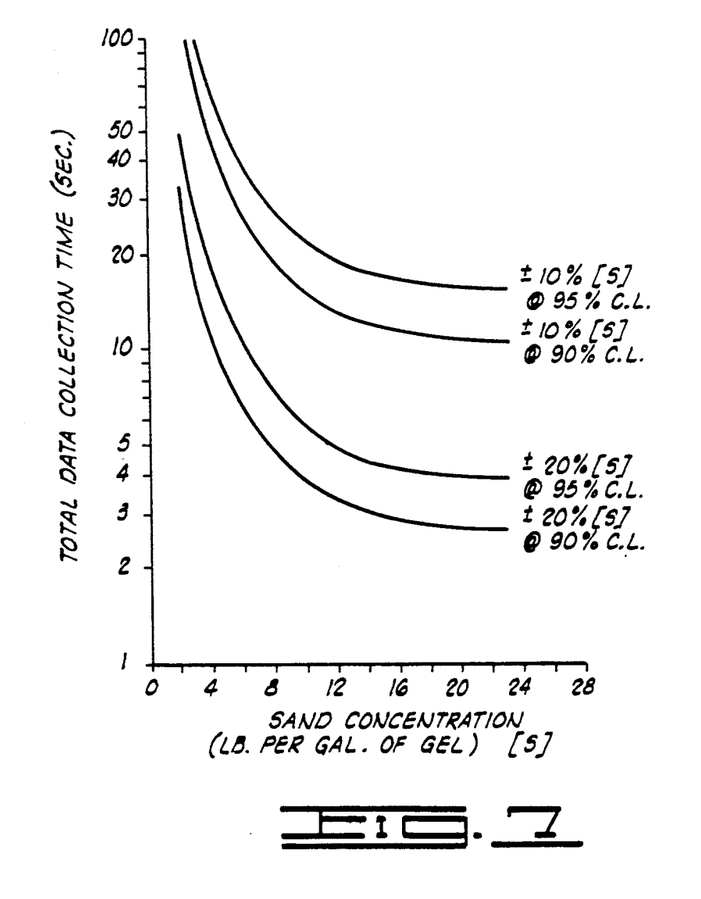
FIG. 7 is a graph of experimental calculated data collection time as a function of sand concentration, [S], and desired precision at a given confidence level (c.l.).

From the response function determined using the 0.5" gap, the total time needed to collect data to achieve a given precision at a given confidence level (c.l.) was calculated for a given gravel concentration. The results of these calculations are illustrated in FIG. 7. For example, at 12# (pounds) gravel per gallon of gel, the required collection time for a precision of ±10% of the gravel concentration, at a 90% c.l., would be 13 seconds. The plot shows other combinations of precision and confidence levels that could be used. As the gravel concentration decreases, the collection time required increases rapidly because the differential required by the precision decreases, i.e., 10% of 2# gravel is more difficult to detect that 10% of 20# gravel.

The results of the spatial resolution measurements indicate that approximately 85% of the counts are due to neutron interactions in the sample material that consist of a 4" wide section. This section is centered on a line located at the junction of the neutron source and the neutron detector and running parallel to the long axis of the detector. Therefore, the spatial resolution of this test apparatus is approximately 4".

Figure 9:
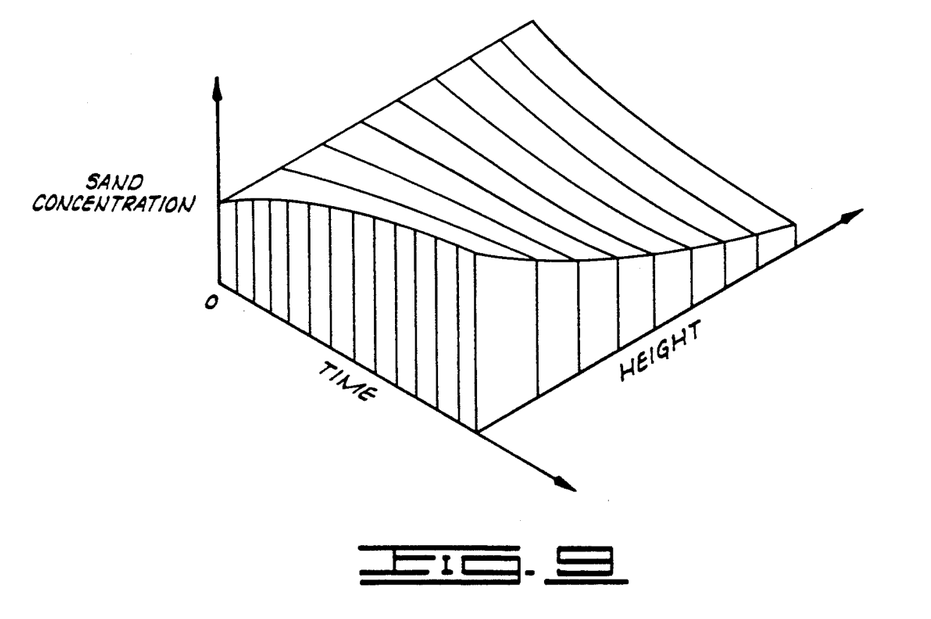
FIG. 9 illustrates a three-dimensional plot of information obtainable with the present invention, namely, sand concentration as a function of settling time and height.

Referring to FIG. 8, a contemplated preferred test model would comprise a 250 mCi AmBe neutron source 58 (0.75"×1.0") and a 2"×6" He-3 neutron detector 60 mounted in an apparatus that would move from top to bottom of a vertical slab. The vertical slab would include two 0.25"×12"×15' steel plates 62, 64 separated by 0.5". The neutron source and detector would be surrounded by a 6" radius poly-boron hemisphere 66 for shielding. A 0.020" cadmium liner 68 lines the hemisphere 66 so that the liner 68 is between facing surfaces of the hemisphere 66 and the plate 64 and between facing surfaces of the hemisphere 66 and the source 58 and detector 60 as viewed in FIG. 8 (i.e., not between the plate 64 and the source 58 or the detector 60). A similar shielding hemisphere 70 would be located on the opposite side of the slab and travel up and down the slab with the other hemisphere. According to previous measurements, the total dose equivalent rate, neutron plus gamma, outside the hemispheres would be approximately 1 mrem/h (10 uSv/h). The system would then be calibrated by flowing known concentrations of gravel/gel through the system and obtaining a calibration graph of count rate versus gravel concentration. This information would then be stored in a computer (e.g., a personal computer) which would then read out the gravel concentration of an unknown solution when it is introduced into the system. The information that could be obtained from this method is illustrated in FIG. 9. This includes a three-dimensional plot where the gravel concentration is plotted as a function of time and vertical height.

Thus, the present invention is well adapted to carry out the objects and attain the ends and advantages mentioned above as well as those inherent therein. While preferred embodiments of the invention have been described for the purpose of this disclosure, changes in the performance of steps can be made by those skilled in the art, which changes are encompassed within the spirit of this invention as defined by the appended claims.

What is claimed is:

1. A method of evaluating a gravel pack slurry, comprising:
   placing the gravel pack slurry in a channel;
   emitting fast neutrons at the placed slurry from outside the channel so that fast neutrons are thermalized in response to the gravel pack slurry;
   detecting from outside the channel neutrons which have been thermalized in the gravel pack slurry in the channel;
   providing a count representative of the detected neutrons; and
   determining a characteristic of the gravel pack slurry in response to the count;
   wherein said emitting includes emitting fast neutrons from a plurality of sources of fast neutrons disposed at respective discrete fixed locations relative to the channel, and wherein said detecting includes detecting thermalized neutrons with a plurality of thermalized neutron detectors, each disposed with a respective one of the sources of fast neutrons at a respective one of the discrete fixed locations; and wherein the discrete fixed locations are around a circumference of the channel.

2. A method of evaluating a gravel pack slurry including gravel and a carrier medium, comprising:
   determining, at a plurality of locations, thermal neutron responses of the gravel pack slurry to fast neutrons emitted into the gravel pack slurry; and
   comparing the responses to determine the relative distribution of gravel and carrier medium at the plurality of locations.

3. A method as defined in claim 2, wherein the gravel pack slurry is flowing.

4. A method as defined in claim 2, wherein said determining includes moving a source of fast neutrons and a detector of thermal neutrons relative to the gravel pack slurry.

5. A method as defined in claim 2, wherein said determining includes sensing thermal neutrons with a plurality of thermal neutron detectors fixed at the plurality of locations.

6. A method as defined in claim 5, wherein said determining includes emitting fast neutrons from a single source of fast neutrons relative to said plurality of thermal neutron detectors.

7. A method as defined in claim 5, wherein said determining includes emitting fast neutrons from a plurality of sources of fast neutrons corresponding to the plurality of thermal neutron detectors.

8. A method of determining a gravel settling rate for a gravel pack slurry including gravel and a carrier medium, comprising:
   (a) emitting fast neutrons into the gravel pack slurry so that fast neutrons are thermalized in response to hydrogen in the gravel pack slurry, wherein the gravel and carrier medium are initially mixed within the gravel pack slurry;
   (b) detecting thermalized neutrons from the gravel pack slurry;
   (c) continuing steps (a) and (b) from a first time, at which a substantially constant relatively low level of thermalized neutrons is detected, until a second time, at which a substantially constant relatively high level of thermalized neutrons is detected; and
   (d) determining the gravel settling rate in response to the difference between the first time and the second time.

* * * * *